(12) United States Patent
Baker (10) Patent No.: US 6,641,695 B2
(45) Date of Patent: Nov. 4, 2003

(54) DRY FORMED COMPOSITE WITH CUT AND PLACE LAYERS

(75) Inventor: Andrew Baker, Alpharetta, GA (US)

(73) Assignee: Paragon Trade Brands, Inc., Norcross, GA (US)

(*) Notice: Subject to any disclaimer, the term of this patent is extended or adjusted under 35 U.S.C. 154(b) by 17 days.

(21) Appl. No.: 10/074,215

(22) Filed: Feb. 14, 2002

(65) Prior Publication Data
US 2003/0150551 A1 Aug. 14, 2003

(51) Int. Cl.⁷ .......................... A61F 13/15; B32B 31/08; B32B 31/18
(52) U.S. Cl. ................. 156/265; 156/269; 156/510; 156/521; 156/552; 264/112; 264/122
(58) Field of Search .............................. 156/263–265, 156/302–303, 362, 510, 517, 519, 521, 269, 552; 264/109, 112, 122

(56) References Cited

U.S. PATENT DOCUMENTS

| | | | |
|---|---|---|---|
| 4,100,324 A | 7/1978 | Anderson et al. |
| 4,289,130 A | 9/1981 | Usami et al. |
| 4,646,362 A | 3/1987 | Heran et al. |
| 5,336,552 A | 8/1994 | Strack et al. |
| 5,350,370 A | 9/1994 | Jackson et al. |
| 5,415,716 A | 5/1995 | Kendall |
| 5,425,725 A | 6/1995 | Tanzer et al. |
| 5,436,066 A | 7/1995 | Chen |
| 5,486,167 A | 1/1996 | Dragoo et al. |
| H1565 H | 7/1996 | Brodof et al. |
| 5,536,264 A | 7/1996 | Hsueh et al. |
| H1585 H | 8/1996 | Ahr |
| 5,650,222 A | 7/1997 | DesMarais et al. |
| 5,681,300 A | 10/1997 | Ahr et al. |
| 5,695,486 A | 12/1997 | Broughton et al. |
| 5,713,881 A | 2/1998 | Rezai et al. |
| 5,849,002 A | 12/1998 | Carlos et al. |
| 5,853,402 A | 12/1998 | Faulks et al. |
| 5,863,288 A | 1/1999 | Baker |
| 5,882,464 A | 3/1999 | Theisgen et al. |
| 5,891,120 A | 4/1999 | Chmielewski |
| 5,922,165 A | 7/1999 | Bitowft et al. |
| 5,983,650 A | 11/1999 | Ando et al. |
| 6,059,710 A | 5/2000 | Rajala et al. |
| 6,068,620 A | 5/2000 | Chmielewski |
| 6,074,333 A | 6/2000 | Rajala et al. |
| 6,095,218 A | 8/2000 | Delmolino et al. |
| 6,149,755 A | 11/2000 | McNichols et al. |
| 6,165,306 A | 12/2000 | Rajala |
| 6,239,565 B1 | 5/2001 | Alvaro et al. |
| 6,372,953 B1 | 4/2002 | Young et al. |
| 6,503,854 B1 | 1/2003 | Abuto et al. |

Primary Examiner—Sam Chuan Yao
(74) Attorney, Agent, or Firm—Hunton & Williams

(57) ABSTRACT

The present invention generally relates to a method and apparatus for forming an absorbent garment and an absorbent composite core. The absorbent composite core preferably is comprised of at least four layers, whereby two of the layers are outer layers, (an upper layer and a lower layer), one of the inner layers is a central fibrous layer containing a mixture of tow fibers and SAP, and the other inner layer is at least one layer selected from an acquisition layer, a distribution layer, an additional fibrous layer optionally containing SAP, a wicking layer, a storage layer, a dryness layer, a softness layer, or combinations and fragments thereof.

63 Claims, 4 Drawing Sheets

DRY FORMED COMPOSITE WITH CUT AND PLACE LAYERS

FIELD OF THE INVENTION

The present invention relates generally to methods of making an absorbent core for a disposable absorbent garment. More particularly, the invention relates to a method of making an absorbent core comprising one or more laminates in which one of the layers of the laminate or laminates contains a mixture of tow fibers and superabsorbent polymer (SAP), and at least an additional layer of the laminate is a layer that has been cut-and-placed on an outer sheet of the laminate. The additional layer preferably is selected from a wicking layer, storage layer, acquisition layer, wicking/distribution layer, dryness layer, or combinations of these layers, or fragmented layers thereof.

BACKGROUND OF THE INVENTION

Disposable absorbent garments such as infant diapers or training pants, adult incontinence products and other such products, typically were constructed with a moisture-impervious outer backing sheet, a moisture-pervious body-contacting inner liner sheet, and a moisture-absorbent core sandwiched between the liner and backing sheets. Much effort has been expended to find cost-effective materials for absorbent cores that display favorable liquid absorbency and retention. Superabsorbent materials in the form of granules, beads, fibers, bits of film, globules, etc., have been favored for such purposes. Such superabsorbent materials generally are polymeric gelling materials that are capable of absorbing and retaining even under moderate pressure large quantities of liquid, such as water and body wastes, relative to their own weight.

The superabsorbent material generally is a water-insoluble but water-swellable polymeric substance capable of absorbing water in an amount which is at least ten times the weight of the substance in its dry form. In one type of superabsorbent material, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

Adequate absorbency of liquid by the absorbent core at the point of initial liquid contact and rapid distribution of liquid away from this point is necessary to ensure that the absorbent core has sufficient capacity to absorb subsequently deposited liquids. Previously known absorbent cores have thus attempted to absorb quickly and distribute large quantities of liquids throughout the absorbent core while minimizing gel blocking during absorption of multiple doses of liquid.

It is known to provide absorbent laminates comprised of, for example, an upper layer, a lower layer, and a central fibrous layer containing from 50% to 95% by weight SAP. U.S. Pat. No. 6,068,620, the disclosure of which is incorporated herein by reference in its entirety and in a manner consistent with the present disclosure, discloses that the upper and lower layers are comprised of tissue, airlaid fluff pulp/or-nthetic non-woven fibrous layers. The upper and lower layers are said to assist in maintaining the integrity of the core, the laminate layered arrangement is said to minimize gel blocking, and the laminate can be folded in various configurations. It also is known to provide a composite absorbent structure having a wicking layer bonded to the absorbent layer with a bonding agent such that the absorbent structure has a Contact Intimacy Ratio. U.S. Pat. No. 6,239,565, the disclosure of which is incorporated by reference herein in its entirety, discloses an absorbent composite having a wicking layer that has a vertical wicking flux value, an absorbent liquid retention layer, and a bonding agent.

It also is known to provide absorbent cores comprised of differing materials in an attempt to maximize comfort and efficiency of the core, and to provide areas having varying degrees of absorbency. U.S. Pat. No. 5,849,002, the disclosure of which is incorporated by reference herein in its entirety, discloses absorbent cores having three zones: (i) one zone for receiving fluids; (ii) one zone for distributing and storing fluids; and (iii) one zone for preventing leakage. U.S. Pat. No. 5,853,402, the disclosure of which is incorporated by reference herein in its entirety, discloses composite absorbent cores comprising at least an absorbent material and a porous resilient material. Other composite, zoned, or multi-component cores are disclosed in, for example, U.S. Pat. Nos. 5,681,300 (blended absorbent core), U.S. Pat. No. 5,882,464 (crimping to join two absorbent structures), U.S. Pat. No. 5,891,120 (varying SAP concentration throughout core), U.S. Pat. Nos. 5,425,725 and U.S. Pat. No. 5,983,650 (multiple fiber free SAP pockets in core), and U.S. Pat. No. 5,922,165 (method of joining outer layers with absorbent core disposed between the outer layers). The respective disclosures of each of these documents are incorporated by reference herein in their entirety.

It also is known to effect synchronous, in-line placement of absorbent core pads on a continuous web of material, as described in U.S. Pat. No. 5,415,716, the disclosure of which is incorporated by reference herein in its entirety. It further is known that graphics can be applied in registration on a moving sheet of material that ultimately is used in an absorbent garment by controlling the timing of placing the discrete graphic material. A number of documents describe placing graphic materials in registration on a moving web, including U.S. Pat. Nos. 6,165,306, 6,149,755, 6,095,218, 6,074,333, and 6,059,710, the disclosures of each of which are incorporated by reference herein in their entireties.

The description herein of advantages and disadvantages of various features, embodiments, methods, and apparatus disclosed in other publications is in no way intended to limit the present invention. Indeed, certain features of the invention may be capable of overcoming certain disadvantages, while still retaining some or all of the features, embodiments, methods, and apparatus disclosed therein.

SUMMARY OF THE INVENTION

It would be desirable to provide an absorbent garment having an improved ability to retain fluids and consequently, to prevent leakage. It also would be desirable to provide an absorbent core that includes an increased amount of superabsorbent polymer, (SAP) but at the same time does not suffer from gel blocking to any appreciable extent. It also would be desirable to provide an absorbent core that has the above mentioned characteristics, and in addition has improved acquisition of fluids, and improved distribution and storage of fluids that insult the core.

It is believed that many of these advantages, as well as others not specifically mentioned herein, can be achieved by including an additional layer(s), or fragments thereof in an absorbent composite that includes an upper layer, a lower layer, and a central fibrous layer that comprises a mixture of tow fibers and SAP. It would be desirable to provide a method that can adequately place the additional layer(s), or fragments thereof, in the absorbent composite in the appropriate position to provide the maximum benefit thereof.

It therefore is a feature of an embodiment of the invention to provide a method of making an absorbent garment having an improved ability to retain fluids. It is an additional feature of an embodiment of the invention to provide a method of making an absorbent garment that includes an absorbent composite core having high dry and wet strength for processing and in-use performance, whereby the absorbent composite core includes an upper layer, a lower layer, a central absorbent layer that includes a mixture of tow fibers and SAP particles as a substantial percentage of its basis weight, and an additional layer(s) or fragments thereof. The additional layer is disposed within the absorbent composite core by a synchronous in-line placement thereof onto one of the upper and/or lower layers. The absorbent composite core has good fluid acquisition, distribution, and storage characteristics.

These and other features of the invention can be achieved by a method of making an absorbent composite core that includes providing to a core forming station an upper layer, a lower layer, a central absorbent layer comprising a mixture of tow fibers and SAP, and an additional layer. At least one additional layer is cut and placed on one of the upper and/or lower layer by a synchronous in-line placement method. The central absorbent layer is formed at the core forming station whereby the tow fibers and SAP are mixed and disposed between the upper and lower layer in such a fashion that the additional layer also is disposed between the upper and lower layers. The additional layer is one or more layers selected from an acquisition layer, a distribution layer, an additional fibrous layer optionally containing SAP, a wicking layer, a storage layer, a dryness layer, or combinations and fragments of these layers.

In accordance with an additional feature of an embodiment of the invention, there is provided a method of making an absorbent article that includes providing to a garment forming station a top sheet material and a back sheet material. The method also include preparing an absorbent composite core as described above, and disposing the absorbent composite core between the top sheet material and the back sheet material.

In accordance with an additional feature of an embodiment of the invention, there is provided an apparatus for making an absorbent composite core that includes a composite core forming station, an upper layer supply mechanism for supplying an upper layer to the composite core forming station, and a lower layer supply mechanism for supplying a lower layer to the composite core forming station. The apparatus further includes a tow supply mechanism, a device for opening the tow operatively associated therewith, and a SAP feeding device. The SAP feeding device and the device for opening tow are positioned relative to the composite core forming station, upper layer supply mechanism, and lower supply mechanism such that they respectively feed the SAP and opened tow to the composite core forming station in between the upper layer and the lower layer.

The apparatus further includes a cut-and-place apparatus for effecting synchronous in-line placement of an additional layer or layer. The cut-and-place apparatus is controlled to cut one or more additional layers that are fed to the cut-and-place device at a first speed, and then place the cut additional layer(s) on either the upper layer or lower layer at a second speed that is different from the first speed. The cut-and-place apparatus therefore is positioned relative to either the upper layer supply mechanism or the lower layer supply mechanism to effect placement thereon of the one or more additional layers in such a fashion that the one or more additional layers is disposed between the upper and lower layer at the composite core forming station.

In accordance with an additional feature of an embodiment of the invention, there is provided an apparatus for making an absorbent garment that includes a garment forming station, the above-described apparatus for making an absorbent composite core, and a mechanism for feeding the absorbent composite core to the garment forming station. The apparatus further includes a top sheet supply mechanism for supplying a top sheet material to the garment forming station, and a back sheet supply mechanism for supplying a back sheet material to the garment forming station. The garment forming station forms the absorbent garment by disposing the absorbent composite core between the top sheet material and the back sheet material.

In addition to the foregoing advantages, the absorbent garment having an absorbent composite core comprising one or more SAP-containing central fibrous layers improves the comfort and fit of the garment. Further, due to the thinness of the resulting product, less packaging material is needed for the same amount of product, and shipping and handling costs are lowered.

These and other features and advantages of the preferred embodiments will become more readily apparent when the detailed description of the preferred embodiments is read in conjunction with the attached drawings.

DETAILED DESCRIPTION OF THE PREFERRED EMBODIMENTS

As used herein, the terms "absorbent garment," "absorbent article" or simply "article" or "garment" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary"

garments), or they may comprise replaceable inserts or other interchangeable parts.

The present invention may be used with all of the foregoing classes of absorbent garments, without limitation, whether disposable or otherwise. The embodiments described herein provide, as an exemplary structure, a diaper for an infant, however this is not intended to limit the claimed invention. The invention will be understood to encompass, without limitation, all classes and types of absorbent garments, including those described herein. Preferably, the absorbent core is thin in order to improve the comfort and appearance of a garment.

Throughout this description, the expressions "upper layer" and "lower layer" that refer to the layers surrounding the absorbent laminate core of the invention are used merely to describe one layer above the core, and one layer below the core. The upper layer need not always remain vertically above the core, and the lower layer need not always remain vertically below the core. Indeed, many embodiments of the invention encompass various configurations of the absorbent laminate core whereby the laminate is folded in such a manner that the upper layer ultimately becomes the vertically highest and vertically lowest layer at the same time. Other configurations are contemplated within the context of the present invention.

Figure 1:
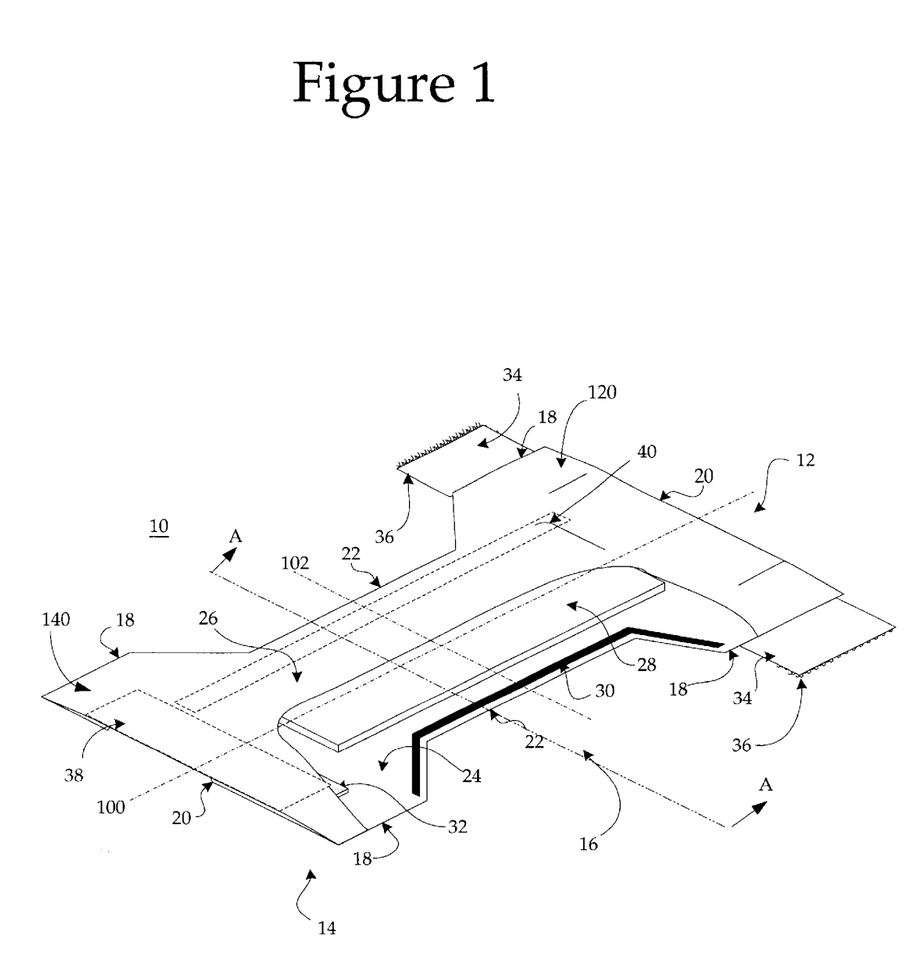
FIG. 1 is a partially cut-away view of an embodiment of the present invention, shown with elastic members fully stretched in the main portion of the garment.
Figure 2:
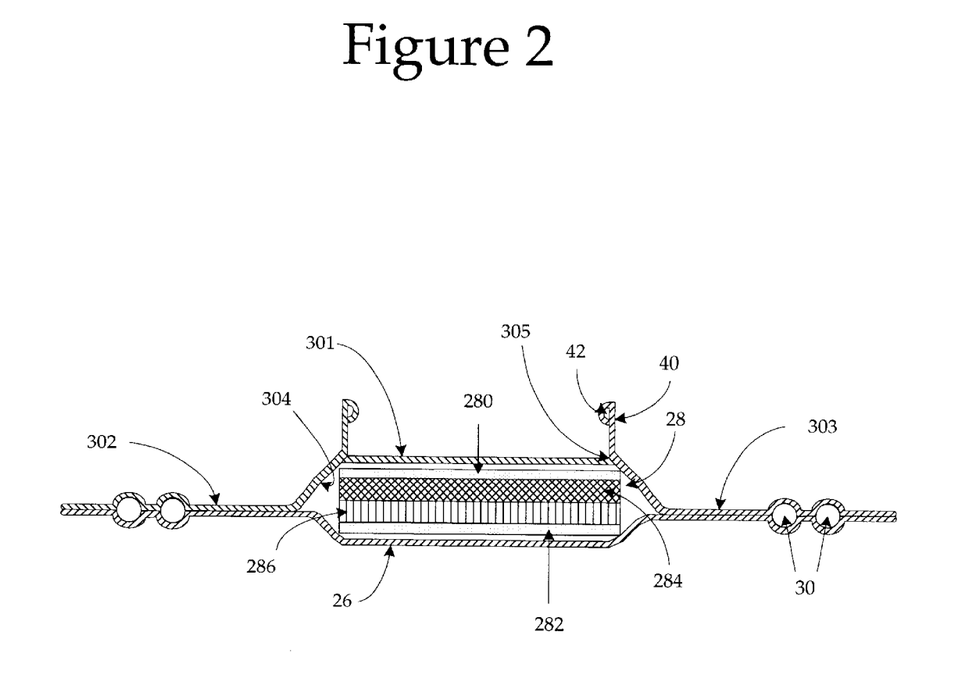
FIG. 2 is a cross-sectional view of the absorbent garment in FIG. 1 taken along line A—A, illustrating one embodiment for the absorbent laminate core of the invention.

Throughout this description, the expressions "fragmented layer" or "non-continuous layer" denote a layer that does not exist as a unitary article across the relevant cross-section of the absorbent article. For example, absorbent composite core 28, as shown in FIGS. 1 and 2, is a unitary article along the longitudinal 100 and lateral 102 axis, throughout its relevant cross-section. A fragmented layer would only exist in certain portions either laterally (as shown in FIGS. 3a–3g) or longitudinally (not shown). These types of layers enable imparting specific properties to specific areas of the absorbent garment where those properties are needed most.

The term "component" can refer, but is not limited to designated selected regions, such as edges, corners, sides or the like; structural members, such as elastic strips, absorbent pads, stretchable layers or panels, layers of material, or the like; or a graphic.

Throughout this description, the term "disposed" and the expressions "disposed on," "disposing on," "disposed in," "disposed between" and variations thereof (e.g., a description of the article being "disposed" is interposed between the words "disposed" and "on") are intended to mean that one element can be integral with another element, or that one element can be a separate structure bonded to or placed with or placed near another element. Thus, a component that is "disposed on" an element of the absorbent garment can be formed or applied directly or indirectly to a surface of the element, formed or applied between layers of a multiple layer element, formed or applied to a substrate that is placed with or near the element, formed or applied within a layer of the element or another substrate, or other variations or combinations thereof.

Throughout this description, the terms "top sheet" and "back sheet" denote the relationship of these materials or layers with respect to the absorbent composite core. It is understood that additional layers may be present between the absorbent composite core and the top sheet and back sheet, and that additional layers and other materials may be present on the side opposite the absorbent composite core from either the top sheet or the back sheet.

Throughout this description, the expression "tow fibers" relates in general to any continuous fiber. Tow fibers typically are used in the manufacture of staple fibers, and preferably are comprised of synthetic thermoplastic polymers. Usually, numerous filaments are produced by melt extrusion of the molten polymer through a multi-orifice spinneret during manufacture of staple fibers from synthetic thermoplastic polymers in order that reasonably high productivity may be achieved. The groups of filaments from a plurality of spinnerets typically are combined into a tow which is then subjected to a drawing operation to impart the desired physical properties to the filaments comprising the tow. It is believed that tow adds surface area to the core, which improves capacity and capillarity as well as surfaces for glue to attach SAP. Tow also is believed to add wet integrity to the core that would otherwise be very poor, as well as add dry integrity that helps with the manufacturing processes.

The expression "absorbent composite core" is used herein to denote an absorbent core that contains at least an upper layer, a lower layer, and a central fibrous layer disposed between the upper layer and the lower layer. The absorbent composite core of the present invention also includes at least one or more additional layers, or combinations and fragments thereof, disposed between the upper layer and the lower layer.

The present invention relates generally to absorbent articles, and in particular to a method of making an absorbent article that contains a top sheet, a back sheet, and an absorbent composite core disposed between the top sheet and the back sheet. The absorbent composite core of the invention preferably is comprised of at least four layers, whereby two of the layers are outer layers, (i.e., an upper and a lower layer) and one of the inner layers is a central fibrous layer containing tow fibers and SAP. The absorbent composite core further includes as the at least one other inner or central layer, a layer selected from an acquisition layer, a distribution layer, an additional fibrous layer optionally containing SAP, a wicking layer, a storage layer, a dryness layer, or combinations and fragments of these layers. The at least two inner layers are disposed between an upper layer and a lower layer.

The absorbent article of the invention preferably has a front waist region, a rear waist region and a crotch region positioned between the front and rear waist regions. The front waist region and rear waist region can be associated with one another to form a waist opening, and two leg openings. Those skilled in the art recognize that "front" and "rear" in the context of the invention denote for clarity purposes only the front and rear of a user, and that the absorbent article could be reversed whereby the previously described "front" portion becomes the rear portion, and vice versa.

Leg elastics preferably are provided along the leg openings for securely holding the leg openings against the thighs of the wearer to improve containment and fit. A fastening system, either resealable or permanent, preferably holds the absorbent article around the wearer's waist. The fastening system assists in associating the front waist region with the rear waist region. A pair of stand-up leg gathers or waist containment flaps may be attached to or formed from the body's side surface of the top sheet.

Other non-SAP-containing roll good materials such as latex or thermally bonded airlaid fluff pulp, (e.g., roll good available from Walkisoft, Merfin or Fort James), or synthetic spunbonded, carded, or hydro-entangled nonwoven may be positioned above and below the absorbent composite core. At least the central fibrous layer of the absorbent composite core preferably contains 30–95% by weight particulate or fibrous SAP and at least one other fibrous or particulate material that is comprised of tow fibers.

The invention now will be described with reference to the attached drawings illustrating preferred embodiments of the invention. For clarity, features that appear in more than one Figure have the same reference number in each Figure.

FIG. 1 is a partially cut away depiction of an exemplary embodiment of an absorbent garment 10 (preferably a disposable absorbent garment) that can be made in accordance with the present invention. The embodiment shown in FIG. 1 is an infant's diaper, however, this depiction is not intended to limit the invention, and those skilled in the art appreciate that the invention covers other types of absorbent articles. For simplicity, however, the invention will be described with reference to an infant's diaper. The garment 10 of FIG. 1 is depicted in a generally flattened position, with the body-facing side facing down, and with the various elastic components depicted in their relaxed condition with the effects of the elastics removed for clarity (when relaxed, the elastics typically cause the surrounding material to gather or "shirr"). In the flattened position, the garment 10 may have a generally hourglass shaped structure, but it may also have any other shape suitable for the given application, such as a rectangular shape, a trapezoidal shape, a "T" shape, and the like.

As used herein, the longitudinal axis 100 of the garment is the dimension of the garment corresponding to the front-to-rear dimension of the user, and the lateral axis 102 of the garment is the dimension corresponding to the side-to-side dimension of the user.

In use, the invention comprises a pant-like garment 10 having a waist-encircling region and a crotch region. The waist-encircling region may comprise a first waist region 12, disposed adjacent to, for example, the back waist region of a wearer's body, and a second waist region 14, disposed adjacent to, for example, the front waist region of a wearer's body. The first and second waist regions 12, 14, may correspond to the front and back of the wearer's body, respectively, depending on whether garment 10 is attached in front of or behind the subject wearer. The first and second waist regions are joined together at or near their lateral edges 18, causing the longitudinally distal edges 20 of the garment 10 to form the perimeter of a waist opening. A crotch region 16 extends between the first and second waist regions 12, 14, and the crotch edges 22 form the perimeter of a pair of leg openings, when the garment 10 is placed on a subject wearer.

The garment 10 preferably comprises a top sheet material 24, ("top sheet") and a back sheet material 26, ("back sheet") which may be substantially coterminous with the top sheet 24. When the garment 10 is being worn, the top sheet 24 faces the wearer's body, and the back sheet 26 faces away from the wearer. An absorbent composite core 28 preferably is disposed between at least a portion of the top sheet 24 the back sheet 26.

An embodiment of the present invention may further comprise various additional features. One or more pairs of elastic gathers 30 may extend adjacent the crotch edges 22. The garment 10 may also comprise one or more waste containment systems, such as inboard standing leg gathers 40, which preferably extend from the second waist region 14 to the first waist region 12 along opposite sides of longitudinal center line 100 (only one standing leg gather system 40 is shown in FIG. 1 for purposes of clarity). One or both of the first and second waist regions 12, 14 may also be equipped with strips of elastic waist foam 32 or other elastically extensible material, which help contract the garment around the wearer's waist, providing improved fit and leakage prevention.

The absorbent garment 10 also preferably includes fastening elements to enable attachment of the first waist region 12 to second waist region 14. Fastening elements preferably include a pair of tabs 34 that extend laterally away from opposite lateral edges 18 of the first waist region 12 of the garment 10. The tabs 34 may comprise an elastically extensible material (not shown), and may be designed to stretch around a wearer's waist to provide improved fit, comfort, and leakage protection. Such elasticized tabs 34 may be used in conjunction with, or in lieu of, waist foam 32, or other elastically extensible materials 32.

At least one fastening mechanism 36 (collectively referred to as "fastener 36") is attached to each tab 34 for attaching the tab to the second waist region 14, thereby providing the garment 10 with a pant-like shape, and enabling garment 10 to be fixed or otherwise fitted on the wearer. The fasteners 36 may attach to one or more target devices 38 located in the second waist region 14.

Although not shown in the drawings, the absorbent garment 10 may also include grips attached along one of its edges proximal to each tab 34 to enable a caregiver to pull the grips, and not on the ends of the tabs 34, around the wearer and over the target devices 38 to thereby secure the fasteners 36 to the one or more target devices 38.

The various parts of the garment 10 can be attached to one another or associated with one another to form a structure that preferably maintains its shape during the useful life of the garment 10. As used herein, the terms "attached," "joined," "associated," and similar terms encompass configurations whereby a first part is directly joined to a second part by affixing the first part directly to the second part, by indirectly joining the first part to the second part through intermediate members, and by fixing the relative positions of various parts by capturing parts between other parts. Those skilled in the art will appreciate that various methods or combinations of methods may be used to securely join the respective parts of the garment 10 to one another.

The top sheet 24 and back sheet 26 may be constructed from a wide variety of materials known in the art. The invention is not intended to be limited to any specific materials for these components. The top sheet 24 and back sheet can be shaped and sized according to the requirements of each of the various types of absorbent garment, or to accommodate various user sizes. In an embodiment of the invention in which the garment 10 is a diaper or an adult incontinence brief, the combination of top sheet 24 and back sheet 26, may have an hourglass shape, as seen in FIG. 1, or may have a rectangular, trapezoidal, "T" shape, or other shape.

Due to the wide variety of backing and liner sheet construction and materials currently available, the invention is not intended to be limited to any specific materials or constructions of these components. The back sheet 26 preferably is made from any suitable pliable liquid-impervious material known in the art. Typical back sheet materials include films of polyethylene, polypropylene, polyester, nylon, and polyvinyl chloride and blends of these materials. For example, the back sheet can be made of a polyethylene film having a thickness in the range of 0.02–0.04 mm. The back sheet 26 may be pigmented with, for example, titanium dioxide, to provide the garment 10 with a pleasing color or to render the back sheet 26 opaque enough that exudates being contained by the garment 10 are not visible from outside the garment. In addition, the back sheet 26 may be formed in such a manner that it is opaque, for example, by using various inert components in the polymeric film and then biaxially stretching the film. Other back sheet materials will be readily apparent to those skilled in the art. The back sheet 26 preferably has sufficient liquid imperviousness to prevent any leakage of fluids. The required level of liquid imperviousness may vary between different locations on the garment 10.

The back sheet 26 may further comprise separate regions having different properties. In a preferred embodiment, portions of the back sheet 26 are air-permeable to improve the breathability, and therefore comfort, of the garment 10. The different regions may be formed by making the back sheet 26 a composite of different sheet materials, chemical treatment, heat treatment, or other processes or methods known in the art. Some regions of the back sheet 26 may be fluid pervious. In one embodiment of the invention, the back sheet 26 is fluid impervious in the crotch 16, but is fluid pervious in portions of the first and second waist regions 12, 14. The back sheet 26 may also be made from a laminate of overlaid sheets of material.

The moisture-pervious top sheet 24 can be comprised of any suitable relatively liquid-pervious material known in the art that permits passage of liquid there through. Non-woven liner sheet materials are exemplary because such materials readily allow the passage of liquids to the underlying absorbent composite core 28. Examples of suitable liner sheet materials include non-woven spunbond or carded webs of polypropylene, polyethylene, nylon, polyester and blends of these materials.

The back sheet 26 may be covered with a fibrous, non-woven fabric such as is disclosed, for example, in U.S. Pat. No. 4,646,362 issued to Heran et al., the disclosure of which is hereby incorporated by reference in its entirety and in a manner consistent with this disclosure. Materials for such a fibrous outer liner include a spun-bonded nonwoven web of synthetic fibers such as polypropylene, polyethylene or polyester fibers; a nonwoven web of cellulosic fibers, textile fibers such as rayon fibers, cotton and the like, or a blend of cellulosic and textile fibers; a spun-bonded nonwoven web of synthetic fibers such as polypropylene; polyethylene or polyester fibers mixed with cellulosic, pulp fibers, or textile fibers; or melt blown thermoplastic fibers, such as macro fibers or micro fibers of polypropylene, polyethylene, polyester or other thermoplastic materials or mixtures of such thermoplastic macro fibers or micro fibers with cellulosic, pulp or textile fibers. Alternatively, the back sheet 26 may comprise three panels wherein a central poly back sheet panel is positioned closest to absorbent composite core 28 while outboard non-woven breathable side back sheet panels are attached to the side edges of the central poly back sheet panel. Alternatively, the back sheet 26 may be formed from microporous poly coverstock for added breathability.

As illustrated in more detail in FIG. 2, the top sheet 24 may be formed of three separate portions or panels. Those skilled in the art will recognize, however, that top sheet 24 need not be made of three separate panels, and that it may be comprised of one unitary item. A first top sheet panel 301 may comprise a central top sheet panel formed from preferably a liquid-pervious material that is either hydrophobic or hydrophilic. The central top sheet panel 301 may be made from any number of materials, including synthetic fibers (e.g., polypropylene or polyester fibers), natural fibers (e.g., wood or cellulose), apertured plastic films, reticulated foams and porous foams to name a few. One preferred material for a central top sheet panel 301 is a cover stock of single ply non-woven material which may be made of carded fibers, either adhesively or thermally bonded, perforated plastic film, spunbonded fibers, or water entangled fibers, which generally weigh from 0.3–0.7 oz./sq. yd. and have appropriate and effective machine direction and cross-machine direction strength suitable for use as a baby diaper cover stock material. The central top sheet 301 panel preferably extends from substantially the second waist region 14 to the first waist region 12, or a portion thereof.

The second and third top sheet panels 302, 303 (e.g., outer top sheet panels), in this alternative embodiment may be positioned laterally outside of the central top sheet panel 301. The outer top sheet panels 302, 303 are preferably substantially liquid-impervious and hydrophobic, preferably at least in the crotch area. The outer edges of the outer top sheet panels may substantially follow the corresponding outer perimeter of the back sheet 26. The material for the outer top sheet portions or panels is preferably polypropylene and can be woven, non-woven, spunbonded, carded or the like, depending on the application.

The inner edges 304 (FIG. 2) of the outer top sheet portions or panels 302, 303 preferably are attached by, e.g., an adhesive, to the outer edges 305 of the inner top sheet portion or panel 301. At the point of connection with the outer edges 305 of the inner top sheet portion or panel 301, the inner edges 304 of the outer top sheet portions or panels 302, 303 extend upwardly to form waste containment flaps 40. The waste containment flaps 40 preferably are formed of the same material as the outer top sheet portions or panels 302, 303, as in the embodiment shown. They are preferably an extension of the outer top sheet portions or panels 302, 303.

The waste containment flaps 40 may be treated with a suitable surfactant to modify their hydrophobicity/hydrophilicity as desired, and they may be treated with skin wellness ingredients to reduce skin irritation. Alternatively, the waste containment flaps 40 may be formed as separate elements and then attached to the body side liner. In this alternative embodiment, the central top sheet portion or panel 301 may extend past the connection point with the waste containment flaps 40, and even extend to the periphery of the back sheet 26.

The waste containment flaps 40 preferably include a portion that folds over onto itself to form a small enclosure. At least one, and depending on the size of the enclosure sometimes more than one, elastic member 42 may be secured in the enclosure in a stretched condition. It is known that when the flap elastic 42 attempts to assume the relaxed, unstretched condition, the waste containment flaps 40 rise above the surface of the central top sheet portion or panel 301.

The top sheet 24 (as well as top sheet portions 301, 302, 303) may be made of any suitable relatively liquid-pervious material currently known in the art or later discovered that permits passage of a liquid therethrough. Examples of suitable top sheet materials include nonwoven spun-bonded or carded webs of polypropylene, polyethylene, nylon, polyester and blends of these materials, perforated, apertured, or reticulated films, and the like. Nonwoven materials are exemplary because such materials readily allow the passage of liquids to the underlying absorbent composite core 28. The top sheet 24 preferably comprises a single-ply non-woven material that may be made of carded fibers, either adhesively or thermally bonded, spunbonded fibers, or water entangled fibers, which generally weigh from 0.3–0.7 oz./sq. yd. and have appropriate and effective machine direction (longitudinal) and cross-machine (lateral) direction strength suitable for use as a top sheet material for the given application. The present invention is not intended to be limited to any particular material for the top sheet 24, and other top sheet materials will be readily apparent to those skilled in the art.

The top sheet 24 may further comprise several regions having different properties. In one embodiment of the present invention, the laterally distal portions of the top sheet 24, especially those used to make second and third top sheet panels 302, 303, preferably are substantially fluid impervious and hydrophobic, while the remainder of the top sheet 24 (e.g., central top sheet panel 301) is hydrophilic and fluid pervious. Different top sheet properties, such as fluid perviousness and hydrophobicity, may be imparted upon the top sheet 24 by treating the top sheet 24 with adhesives, surfactants, or other chemicals, using a composite of different materials, or by other means. The top sheet 24 may also be made from a laminate of overlaid sheets of material. The top sheet 24 also may be treated in specific areas like the crotch region, with skin wellness ingredients such as aloe, vitamin E, and the like.

As noted elsewhere herein, the top sheet 24 and back sheet 26 may be substantially coterminous, or they may have different shapes and sizes. The particular design of the top sheet 24 and back sheet 26 may be dictated by manufacturing considerations, cost considerations, and performance considerations. Preferably, the top sheet 24 is large enough to completely cover the absorbent composite core 28, and the back sheet 26 is large enough to prevent leakage from the garment 10. The design of top sheet 24 and back sheet 26 is known in the art, and a skilled artisan will be able to produce an appropriate top sheet 24 and an appropriate back sheet 26 without undue experimentation.

The top sheet 24 and the back sheet 26 may be associated with one another using a variety of methods known in the art. For example, they may be thermally, ultrasonically, or chemically bonded to one another. They also may be joined using lines of hot melt adhesive or mechanical fasteners, such as thread, clips, or staples. In one embodiment, a hydrophilic adhesive, such as Cycloflex as sold by National Starch, a corporation headquartered in Bridgewater, N.J., is used to join the top sheet 24 to the back sheet 26. The particular joining method may be dictated by the types of materials selected for the top sheet 24 and back sheet 26.

As mentioned above, absorbent garment preferably is provided with leg elastics 30 extending through crotch region 16, adjacent crotch edge 22. The absorbent garment of the invention also preferably is provided with waist elastic material 32 optionally in the first and second waist regions, 12, 14, respectively, to enable and assist in stretching around the wearer. The waist elastics 32 may be similar structures or different to impart similar or different elastic characteristics to the first and second waist regions 12, 14 of the garment. In general, the waist elastics may preferably comprise foam strips positioned at the first and second waist regions 12, 14, respectively. Such foam strips preferably are about ½ to about 1 ½ inches wide and about 3–6 inches long. The foam strips preferably are positioned between the top sheet portions 24 or panels (301, 302, 303) and the back sheet 26. Alternatively, a plurality of elastic strands may be employed as waist elastics rather than foam strips. The foam strips preferably are comprised of polyurethane, but can be any other suitable material that decreases waist band roll over, reduces leakage over the waist ends of the absorbent garment, and generally improve comfort and fit. The first and optional second waist foam strips 32 preferably are stretched 50–150%, preferably 100% more than their unstretched dimension before being adhesively secured between the back sheet 26 and top sheet 24.

Each edge 22 that forms the leg openings preferably is provided with an adjacent leg elastic containment system 30. In the preferred embodiment, three strands of elastic threads (only two strands are shown in FIG. 2 for purposes of clarity) are positioned to extend adjacent to leg openings between the outer top sheet portions or panels 302, 303 and the back sheet 26. Any suitable elastomeric material exhibiting at least an elongation (defined herein as $(L_S-L_R)/L_R$ where $L_S$ is the stretch length of an elastic element and LR is retracted length, multiplied by 100 to obtain percent elongation) in the range of 5%–350%, preferably in the range of 200%–300%, can be employed for the leg elastics 30. The leg elastics 30 may be attached to the absorbent article 10 in any of several ways which are known in the art. For example, the leg elastics 30 may be ultrasonically bonded, heat/pressure sealed using a variety of bonding patterns, or glued to the garment 10. Various commercially available materials can be used for the leg elastics 30, such as natural rubber, butyl rubber or other synthetic rubber, urethane, elastomeric materials such as LYCRA (DuPont), GLOSPAN (Globe) or SYSTEM 7000 (Fulflex).

The fastening elements, preferably a fastening system 34 (e.g., tab 34) of the preferred embodiment, is attached to the first waist region 12, and it preferably comprises a tape tab or mechanical fasteners 36. However, any fastening mechanism known in the art will be acceptable. Moreover, the fastening system 34 may include a reinforcement patch below the front waist portion so that the diaper may be checked for soiling without compromising the ability to reuse the fastener. Alternatively, other absorbent article fastening systems are also possible, including safety pins, buttons, and snaps.

As stated previously, the invention has been described in connection with a diaper. The invention, however, is not intended to be limited to application only in diapers. Specifically, the absorbent laminate cores of the preferred embodiments may be readily adapted for use in other absorbent garments besides diapers, including, but not limited to, training pants, feminine hygiene products and adult incontinence products.

The underlying structure beneath the top sheet 24 may include, depending on the diaper construction, various combinations of elements, but in each embodiment, it is contemplated that the absorbent garment will preferably include an absorbent composite core 28 comprising one or more composites positioned between the top sheet 24 and back sheet 26. The absorbent composite core 28 may take a number of different constructions, depending on how they are configured with respect to one another. However, in each embodiment, one of the layers in the absorbent composite core 28 is a fibrous layer preferably containing about 50–95% by weight SAP, and at least tow fibers.

With particular reference to FIG. 2, and FIGS. 3a–3g, there are illustrated exploded partial cross-sectional schematic views of absorbent composite cores 28 according to various preferred embodiments of the invention. Although the absorbent composite core 28 depicted in the accompanying figures has a substantially rectangular cross-sectional and plan view shape, other shapes may be used, such as a "T" shape or an hourglass shape. The shape of the absorbent composite core 28 may be selected to provide the greatest absorbency with a reduced amount of material. The absorbent composite core 28 may be associated with the top sheet 24, back sheet 26, or any other suitable part of the garment 10 by any method known in the art, in order to fix the absorbent composite core 28 in place. In addition to the respective layers in the absorbent composite core 28, as will be described in greater detail hereinafter, the overall absorbent composite core 28 may be enclosed within a tissue wrapping. Skilled artisans are capable of designing and making a suitable absorbent composite core 28 of the invention, using the guidelines provided below with reference to FIG. 4.

The absorbent composite core 28 may extend into either or both of the first and second waist regions 12, 14. The absorbent composite core 28 of one preferred embodiment of the invention preferably includes at least four (4) layers whereby two of the layers are outer layers, (280, 282, FIG. 2) and one of the inner layers is a central fibrous layer 284 containing a mixture of tow fibers and SAP. The absorbent composite core 28 further includes as the at least one other inner or central layer 286, one or more additional layers selected from a fluid acquisition layer, a distribution layer, an additional fibrous layer optionally containing SAP, a wicking layer, a storage layer, a dryness layer, a softness layer, or combinations and fragments of these layers. The at least two inner layers, the central fibrous layer 284 containing the mixture of tow fibers and SAP, and the at least one other additional inner layer 286, are disposed between the upper layer 280 and the lower layer 282, with the exception that the softness layer may be disposed on the outer surface of upper layer 280 or lower layer 282. Upper layer 280 and lower layer 282 can be made of any suitable material capable of containing the inner layers (284, 286, etc.) of absorbent composite core 28. Preferably, upper layer 280 is hydrophilic and fluid pervious, and lower layer 282 is hydrophobic and fluid impervious. More preferably, upper layer 280 and lower layer 282 are comprised of the same tissue-like material.

In a preferred embodiment, the central fibrous layer 284 of absorbent laminate core 28 comprises super absorbent polymer distributed within a fibrous structure. Central fibrous layers 284 generally of this type are known in the art, and exemplary absorbent cores are described in U.S. Pat. No. 6,068,620 and U.S. Pat. No. 5,281,207, both issued to Chmielewski, and U.S. Pat. No. 5,863,288, issued to Baker, the disclosures of each of which are herein incorporated by reference in their entirety and in a manner consistent with this disclosure.

Certain fibrous and particulate additives preferably are used as constituent elements of an absorbent composite core to maintain high SAP efficiencies when the SAP concentration is in the range of about 50–95%, more preferably about 60–90%, and most preferably about 75–85%. Super absorbent polymers of the surface cross-linked variety are believed to perform best in these composite cores. These additives preferably are constituent elements of the central fibrous layer 284, and they may be added to the additional layer 286 (and optional layers 288). Fibrous additives of central fibrous layer 284 preferably include, but are not limited to, cellulose acetate fibers, rayon fibers, Courtauld's LYOCELL fibers, polyacrylonitrile fibers, surface-modified (hydrophilic) polyester fibers, surface-modified polyolefin/polyester bicomponent fibers, surface-modified polyester/polyester bicomponent fibers, cotton fibers, or blends thereof. Of the foregoing, cellulose acetate is the most preferred fibrous additive for use in central fibrous layer 284. In addition, rayon, Courtauld's LYOCELL, polyacrylonitrile, cotton fibers and cotton linters have similar properties to cellulose acetate and are alternatively preferred. The remaining fibers, surface-modified polyolefin/polyester bicomponent fibers, and surface-modified polyester/polyester bicomponent fibers are also believed to be effective fibrous additives.

The fibrous component of the central fibrous layer 284 most preferably is a crimped tow of cellulose acetate or polyester. Before making the absorbent composite core that includes a tow fiber, the tow fiber typically is unwound and opened, and then fed to the core forming station to provide a fibrous mass of material. Skilled artisans are aware of techniques available to open tow fibers and form the opened fibers into a fibrous mass. Alternatively, the fibrous component of the central fibrous layer 284 may be a low-density roll good made in a separate process. Still further yet, the fibrous component could also be a carded web formed on-line. Optionally, it is advantageous to introduce from about 1–5% of a thermally bondable fiber into the fibrous component of the central fibrous layer 284 for wet strength and core stability in use.

Particulate additives may be added to central fibrous layer 284 in addition to or as a substitute for the foregoing fibrous additives in order to maintain high SAP efficiency. The particulate additives preferably are insoluble, hydrophilic polymers with particle diameters of 100 $\mu$m or less. The particulate additives are chosen to impart optimal separation of the SAP particles. Examples of preferred particulate additive materials include, but are not limited to, potato, corn, wheat, and rice starches. Partially cooked or chemically modified (i.e., modifying hydrophobicity, hydrophilicity, softness, and hardness) starches can also be effective. Most preferably, the particulate additives comprise partially cooked corn or wheat starch because in this state, the corn or wheat are rendered larger than uncooked starch and even in the cooked state remain harder than even swollen SAP. In any event, regardless of the particulate additive chosen, one of the many important criteria is to use particulate additives that are hard hydrophilic materials relative to swollen SAP or which are organic or inorganic polymeric materials about 100 microns in diameter. Fibrous and particulate additives can be used together in these absorbent composites. Examples of SAP/particulate and SAP/fiber/particulate additives include those described in, for example, U.S. Pat. No. 6,068,620.

Any superabsorbent polymer (SAP) now known or later discovered may be used in central fibrous layer 284, so long as it is capable of absorbing liquids. Useful SAP materials are those that generally are water-insoluble but water-swellable polymeric substance capable of absorbing water in an amount that is at least ten times the weight of the substance in its dry form. In one type of SAP, the particles or fibers may be described chemically as having a back bone of natural or synthetic polymers with hydrophilic groups or polymers containing hydrophilic groups being chemically bonded to the back bone or in intimate admixture therewith. Included in this class of materials are such modified polymers as sodium neutralized cross-linked polyacrylates and polysaccharides including, for example, cellulose and starch and regenerated cellulose which are modified to be carboxylated, phosphonoalkylated, sulphoxylated or phosphorylated, causing the SAP to be highly hydrophilic. Such modified polymers may also be cross-linked to reduce their water-solubility.

Commercially available SAPs include a starch modified superabsorbent polymer available under the trade name SANWET® from Hoechst Celanese Corporation, Portsmouth, Va. SANWET® is a starch grafted polyacrylate sodium salt. Other commercially available SAPs include a superabsorbent derived from polypropenoic acid, available under the tradename DRYTECH® 520 SUPERABSORBENT POLYMER from The Dow Chemical Company, Midland Mich.; AQUA KEEP manufactured by Seitetsu Kagaku Co., Ltd.; ARASORB manufactured by Arakawa Chemical (U.S.A.) Inc.; ARIDALL 1125 manufactured by Chemdall Corporation; FAVOR manufactured by Stockhausen Inc.; AQUA KEEP SA60S, manufactured by Seitetsu Kagaku Co., Ltd.; DIAWET, commercially available from Mitsubishi Chemicals, Japan; FLOSORB, available from SNF Floerger, France, AQUALIC, available from Nippon Shokubai, Osaka, Japan.

In accordance with the present invention, the absorbent composite core comprises a mixture of tow fibers and SAP. The tow fiber preferably is a continuous crimped filament tow. This fiber structure has high structural integrity, and as such, is distinct from a matrix of discontinuous fibers described as fluff in the prior art. The high structural integrity enables the production of stronger webs than those formed from discontinuous fibers, which in turn are believed to enable the production of thinner absorbent pads. In addition, the use of such fibers enables the production of ultra low density absorbent cores, when compared to absorbent cores prepared by dispersing SAP particles in fluff.

The tow fiber can be any continuous or discontinuous thermoplastic filament tow fiber that is capable of being opened and used in combination with SAP in an absorbent core. Preferably, cellulose ester tow is used as the fibrous material in central layer 284. Non-limiting examples of suitable cellulose esters include cellulose acetate, cellulose propionate, cellulose butyrate, cellulose caproate, cellulose caprylate, cellulose stearate, highly acetylated derivatives thereof such as cellulose diacetate, cellulose triacetate and cellulose tricaproate, and mixtures thereof such as cellulose acetate butyrate. A suitable cellulose ester will include the ability to absorb moisture, preferably is biodegradable, and is influenced not only by the substituent groups but also by the degree of substitution. The relationship between substituent groups, degree of substitution and biodegradability is discussed in W. G. Glasser et al, Biotechnology Progress, vol. 10, pp. 214–219 (1994), the disclosure of which is incorporated herein by reference in its entirety.

Continuous filament tow useful in the present invention is beneficially moisture-absorbent and biodegradable. Accordingly, cellulose acetate tow is typically preferred for use in the invention. Typically, the denier per fiber (dpf) of the tow fiber will be in the range of about 1 to 9, preferably about 3 to 6. For the same weight product, filaments of lower dpf may provide increased surface area and increased moisture absorption. Total denier may vary within the range of about 20,000 to 60,000, depending upon the process used.

It is particularly preferred in the invention to use tow having crimped filaments. Tow materials having crimped filaments are typically easier to open. Separation of filaments resulting from bloom advantageously results in increased available filament surface area for superabsorbent material immobilization and increased moisture absorption. Gel blocking also may be reduced by using crimped tow in the central layer 284. As therefore may be understood, more crimp is typically better, with in excess of about 20 crimps per inch being usually preferred. Continuous filament, cellulose ester tow having crimped filaments with about 25 to 40 crimps per inch, is commercially available from Celanese Acetate in Charlotte, N.C.

The total basis weights of the absorbent composite core 28 including fibrous materials, SAP, tissue, additional layer (s), and additives, are anywhere from about 200–1,000 grams per square meter. The most preferred total basis weights of the absorbent composite core 28 are about 400–700 grams per square meter. Optionally, about 1–10%, preferably about 5%, by weight of thermally bondable synthetic fibers can be added to the absorbent composite core 28 to impart additional wet strength to the laminate. This will improve the stability of the core during use of the diaper. The preferred synthetic fibers are polyolefin/polyester fibers and polyester/polyester bicomponent fibers.

The absorbent composite cores 28 of the invention preferably include two outer layers 280, 282, a central fibrous layer 284, and at least one additional layer 286. The at least one additional layer can be any layer selected from a fluid acquisition layer, a distribution layer, an additional fibrous layer optionally containing SAP, a wicking layer, a storage layer, a dryness layer, or combinations and fragments of these layers. Such layers may be provided to assist with transferring fluids to the absorbent core 28, handling fluid surges, preventing rewet, containing absorbent material, improving core stability, or for other purposes. Skilled artisans are familiar with the various additional layers that may be included in absorbent article, and the present invention is not intended on being limited to any particular type of materials used for those layers. Rather, the invention encompasses all types of wicking layers, all types of distribution layers, etc., to the extent that type of layer is utilized.

One element that is useful as an additional layer 286 in the absorbent composite core 28 of the invention is a fluid acquisition layer. The fluid acquisition layer typically comprises a hydrophilic fibrous material, and serves to quickly collect and temporarily hold discharged body fluid. A portion of discharged fluid may, depending upon the wearer's position, permeate the acquisition layer and be absorbed by the central fibrous layer 284 in the area proximate to the discharge. However, since fluid is frequently discharged in gushes, the central fibrous layer 284 in such area may not absorb the fluid as quickly as it is discharged. Therefore, the fluid acquisition layer 286 hereof also facilitates transport of the fluid from the point of initial fluid contact to other parts of the absorbent composite core 28. In the context of the present invention, it should be noted that the term "fluid" includes, but is not limited to, liquids, urine, menses, perspiration, and water based body fluids.

The function of the fluid acquisition layer 286 is relatively important. The fluid acquisition layer 286 preferably has sufficient capillary suction to more fully drain the top sheet 24 and yet not exhibit excessive fluid retention to make it difficult for the underlying layer (e.g., central fibrous layer 284) to desorb the acquisition layer 286. The acquisition layer 286 may be comprised of several different materials including nonwoven or woven webs of synthetic fibers including polyester, polypropylene, or polyethylene, natural fibers including cotton or cellulose, blends of such fibers, foams, fluff pulp, apertured films, or any equivalent materials or combinations of materials.

Another useful layer for use in the absorbent composite core 28 of the invention includes a fluid distribution layer 286. Fluid distribution layers 286 of the invention can include any combination or all of three basic components: chemically stiffened, twisted, and curled bulking fibers, high surface area fibers, and binder fibers. In a preferred embodiment of the invention, fluid distribution layer 286 comprises from about 20% to about 80% of the chemically stiffened, twisted, and cured fibers, from about 10% to about 80% of a high surface area fiber, and from 0% to about 50% of a thermoplastic binding means for increasing physical integrity of the web. All percentages herein refer to weight percentages based on total dry web weight. Preferably, the fluid distribution layer 286 will comprise between about 45% and about 60% of chemically stiffened, twisted, and cured fibers, between about 5% and about 15% of a hot melt fibrous binding means, and between about 30% and about 45% high surface area cellulose binding means. More preferably, the fluid distribution layer 286 comprises about 10% thermoplastic binding means, about 45% chemically stiffened, twisted, and cured fibers, and about 45% high surface area fibers.

Chemical additives can also be used as binding means, and are incorporated into the acquisition/distribution layer at levels typically of about 0.2% to about 2.0%, dry web weight basis. The three basic fiber components are described in greater detail in U.S. Pat. No. 5,549,589, the disclosure of which is incorporated by reference herein in its entirety, and in a manner consistent with this disclosure.

Fluid distribution layer 286 also may be comprised of non-woven or woven webs of synthetic fibers, natural fibers, foams, carded, thermal bonded materials, and the like.

Another useful layer in the absorbent composite core 28 of the invention includes a storage layer 286. Such storage layers 286 typically have limited transport and wicking capabilities but high storage or retention capacity, and rely upon the central fibrous layer 284 to distribute incoming fluid over a larger area.

Storage layers or members 286 may be of generally conventional design and composition, selected with regard to the particular application. The storage layer or member 286 may be monolayer or multilayer, homogeneous or stratified, profiled or uniform, etc. Materials suitable for use in such storage layers 286 may be natural or synthetic in origin, woven, non-woven, fibrous, cellular, or particulate, and may include particles, layers, or regions of absorbent polymeric gelling materials. Other preferred materials include fluff pulp and SAP composites, either air laid or wet laid, and high capacity resilient foam materials. Storage layer 286 may also have any desired size and/or shape as may prove suitable for a particular application, including square, rectangular, oval, elliptical, oblong, etc. They may also take on a three-dimensional shape or may be substantially planar in nature.

Another useful layer in absorbent composite core 28 is a wicking layer 286. Wicking layers usually have both fluid acquisition and fluid distribution properties. For example, vertical wicking, which is in general the ability to transport fluids vertically from the top sheet 24 to the absorbent composite core 28, is related in many respects to fluid acquisition. Horizontal wicking, which is in general the ability to transport fluids along the horizontal 100 and vertical 102 axes of FIG. 1, is related in many respects to fluid distribution.

Any conventional wicking materials can be used for the wicking layer 286 of the invention. High internal phase emulsion (HIPE) foams such as those disclosed in U.S. Pat. No. 5,650,222 can be used, braided materials such as those disclosed in H1,585, and other conventional fibrous and strand materials can be used. The disclosures of U.S. Pat. No. 5,650,222 and H1,585 are incorporated by reference here in their entirety, and in a manner consistent with the present invention.

Wicking layer 286 also may be comprised of two or more sublayers containing absorbent materials with differing wicking characteristics. Any of the materials discussed in this context can be used for any and all of the wicking layers 286. In accordance with the embodiment of the invention discussed immediately above, the wicking layer 286 may include a first member that is made of a material that is capable of rapidly transferring, in the z-direction (e.g., orthogonal to the plane formed by horizontal 100 and vertical 102 axes of FIG. 1), body fluid that is delivered to top sheet 24. The first member may be designed to have a dimension narrower than the dimension of the absorbent composite core 28. In this regard, the sides of the first member preferably are spaced away from the longitudinal sides of the absorbent composite core 28 so that body fluid is restricted to the area within the periphery of the first member, before it passes down and is absorbed into central fibrous layer 284 (or second member of the wicking layer 286). This design is believed to enable the body fluid to be combined in the central area of the absorbent composite core 28 and to be wicked downward so that a greater quantity of the central fibrous layer 284 can be utilized.

A suitable material for use as a first member having high wicking capacity in the z-direction, is a material available from Kimberly-Clark Corporation, in Neenah, Wis. known as PRISM. PRISM is described in U.S. Pat. No. 5,336,552, which is hereby incorporated by reference in its entirety, and in a manner consistent with this disclosure. PRISM generally is a nonwoven fabric and comprises extruded multicomponent polymeric strands including first and second polymeric components arranged in substantially distinctive zones across the cross-section of the multicomponent strands and extending continuously along the length of the multicomponent strands. Preferably, the strands are continuous filaments which may be formed by spunbonding techniques. The second component of the strands constitutes at least a portion of the peripheral surface of the multicomponent strands continuously along the length of the multicomponent strands and includes a blend of a polyolefin and an ethylene alkyl acrylate copolymer. Bonds between the multicomponent strands may be formed by the application of heat.

More specifically, the first polymeric component of the multicomponent strands is present in an amount of from about 20 to about 80 percent by weight of the strands, and the second polymeric component is present in an amount from about 80 to about 20 percent by weight of the strands. Preferably, the first polymeric component of the multicomponent strands is present in an amount of from about 40 to about 60 percent by weight of the strands and the second polymeric component is present in an amount from about 60 to about 40 percent by weight of the strands.

The term "strand" as used herein refers to an elongated extrudate formed by passing a polymer through a forming orifice such as a die. Strands include fibers, which are discontinuous strands having a definite length, and filaments, which are continuous strands of material. The nonwoven fabric of the present invention may be formed from staple multicomponent fibers. Such staple fibers may be carded and bonded to form the nonwoven fabric. Preferably, however, the nonwoven fabric of the present invention is made with continuous spunbond multicomponent filaments which are extruded, drawn and laid on a traveling forming surface.

The types of nonwoven materials that may be employed in any of the wicking layers 286 of the invention include powder-bonded-carded webs, infrared bonded carded webs, and through-air-bonded-carded webs. The infrared and through-air bonded carded webs can optionally include a mixture of different fibers, and the fiber lengths within a selected fabric web may be within the range of about 1.0 to 3.0 inch and an average bulk density of about 0.02 g/cc to about 0.06 g/cc.

The first member of wicking layer 286 also may be a nonwoven fibrous web which includes about 75 percent polyester fibers of at least 6 denier, such as PET (polyethylene terephthalate) fibers available from Celanese AG. The polyester fibers have a length ranging from about 1.5 to 2.0 inches in length. The remaining 25 percent of the fibrous web can be composed of bicomponent binder fibers of not more than 3 denier, and preferably about 1.5 denier. The bicomponent fiber length ranges from about 1.5 to 2 inches. Suitable bicomponent fibers are wettable, polyethylene/polypropylene bicomponent fiber, available from Chisso, a business having offices located in Osaka, Japan. The bicomponent fiber can be a composite, sheath-core type with the polypropylene forming the core and polyethylene forming the sheath of the composite fiber. The polyester fibers and bicomponent fibers generally are homogeneously blended together and are not in a layered configuration. The fibers can be formed into a carded web which is thermally bonded, such as by through-air bonding or infrared bonding.

The second member of wicking layer 286 may be positioned vertically below the first member, and it preferably has a higher wicking capacity along the longitudinal 100 and vertical 102 axes of FIG. 1, than the first member. Preferably, the second member has a wicking capacity at least three time greater than the first member. The second member can be equal in width to the first member, but preferably will be wider. It is preferred that the width of the wicking layer 286 in general be the same as or greater than the width of central fibrous layer 284.

The second member can be a hydrophilic material formed from various types of natural or synthetic fibers including cellulose fibers, surfactant treated meltblown fibers, wood pulp fibers, regenerated cellulose, cotton fibers or a blend of other fibers. Preferably, the second absorbent member is a material described in U.S. Pat. No. 4,100,324, and is generally known as coform. Coform is available from the Kimberly-Clark Corporation located in Neenah, Wis. and is generally a nonwoven material having a fabric-like finish and is made up of an airform matrix of thermoplastic polymeric fibers and a multiplicity of individualized wood pulp fibers. The thermoplastic fiber polymers generally have an average diameter of less than 10 microns with the individualized wood pulp fibers dispersed throughout the matrix and serving to space these microfibers from each other. The material is formed by initially utilizing the primary air stream with the meltblown microfibers and the secondary air stream containing wood pulp fibers and merging the two under turbulent conditions to form an integrated air stream along a forming surface. The fiber-like appearance of this material provides a visual appealing absorbent. Also inherent in the coform material is increased resiliency compared to conventional cellulosic absorbents.

Other suitable materials for use as wicking layer 286 include high-density air laid fluff pulps, high-density wet laid fluff pulp, and multi-groove fibers such as 4DG deep groove fiber, available from Eastman Chemical Company, Tennessee, or Clemson University, South Carolina.

Various combinations of layers also may be used as the at least one additional layer 286. For example, additional layer 286 may be comprised of a combination of a wicking layer and a distribution layer. Hence, the additional layer 286 will have both wicking and distribution properties. The at least one additional layer also may be fragmented either along longitudinal axis 100 or vertical axis 102 to maximize the ability of absorbent laminate core 28 to rapidly absorb and retain fluids. Skilled artisans will be capable of designing additional layers 286 to have desired properties by combining various layer attributes, or by fragmenting the layers, using the guidelines provided herein.

The dimensions of additional layer(s) 286 may be the same as or different from the dimensions of central fibrous layer 284 and/or upper layer 280 and lower layer 282. It is preferred that additional layer(s) 286 have a width in the lateral direction (102) of anywhere from about 10 mm to about 100 mm, and preferably from about 25 mm to about 80 mm.

Dryness layers also can be used as the additional layer 286. Dryness layers typically require low hydrophilicity so they stay dry but need to be open structures so they let fluid through, and do not wick fluid (no capillary forces in a hydrophobic layer). This is fine because the other properties typically are handled in the other core components.

Another layer that may be an additional layer 280 used in the present invention is a softness layer. A variety of materials may be used as the softness layer, whose purpose is to add softness to the absorbent garment. Suitable materials include foams, non-woven materials, embossed nonwovens, tissues, and the like. The softness layer also may be disposed on the outer surface of the upper and/or lower layer (280, 282), so that it ultimately is not disposed between the upper layer 280 and the lower layer 282. In addition, the softness layer may be cut and placed on the outer surface of the back sheet 26 or outer layer used to make absorbent garment 10. A variety of configurations of these various layers and core units are shown in FIGS. 13a–13g.

The foregoing absorbent composite cores 28 of the preferred embodiments preferably are made using a dry process, whereby the respective components of the composite core 28 are brought together in a dry state, as opposed to one or more components being in a liquid state. Skilled artisans will be capable of making the absorbent composite cores 28 of the present invention, using the guidelines provided herein.

The absorbent composite core 28 of the invention also may include another central fibrous layer disposed between the upper layer and the lower layer as the additional layer 286. When more than one central fibrous layer is used, different types of SAP may be used in each respective layer, or only one layer may contain SAP and the other be comprised of fibrous material. For example, central fibrous layer 284 that is disposed closest to upper layer 280 may include a rapid acquisition SAP that has relatively low absorbence, whereas the central fibrous layer used as an additional layer 286 disposed closest to lower layer 282 may include slower acquisition SAP with higher absorbency. This configuration would allow liquid to be rapidly absorbed, and then transferred to storage on the bottom of absorbent composite core 28. Skilled artisans again will be capable of designing and fabricating the various central fibrous layers when more than one of such layers are used, using the guidelines provided herein.

When more than one absorbent layer is used in the absorbent composite core 28 of the invention, it is possible to provide for zoned absorbency depending on the type of fiber used, SAP used, and depending on the positioning of the respective layers. For example, a layer of pulp, airlaid, or roll good SAP layer could be cut and placed on the lower layer 282 prior to forming the absorbent core composite. Where that particular layer is placed will have a higher absorptive capacity. Thus, an absorbent laminate core 28 can be designed to have zoned absorbency insofar as the insult point, or central portion of the absorbent laminate core 28 has a higher absorptive capacity than the outer edges.

It is contemplated in the present invention that the absorbent composite core 28 be folded prior to, or as it is disposed between the top sheet 24 and back sheet 26. Absorbent composite core 28 can be folded in any suitable manner, including any and all of those disclosed in U.S. Pat. No. 6,068,620.

Those skilled in the art will appreciate that the absorbent composite core 28 can be folded such that the adjacent sides are touching one another, or so that channels are formed in certain areas. For example, the folded embodiment include a standard "C" fold where the curled ends may be spaced apart to form a channel there between, and the lower edges of the curled ends may be disposed adjacent the upper edges of the bottom portion of the folded article. Alternatively, another absorbent material, or another absorbent composite core 28 may be disposed in the space formed by the standard "C" fold.

The same considerations may be given to the "G" fold and the "U" fold where the absorbent composite core 28 is folded in the form of the letter "G" or "U." The spaces formed by these folds may be filled with another absorbent material, another absorbent composite core 28, or the folds may be made tight enough so that little or no space is formed. Other possible arrangements include a "Z" fold, and a pleated absorbent composite core 28.

The methods and apparatus of the invention will be explained in further detail with reference to FIG. 4. The absorbent composite core 28 preferably is prepared by disposing between an upper layer 280 and a lower layer 282, a central fibrous layer 284 that includes a mixture of tow fibers and SAP, and at least one additional layer 286. The respective components are brought into contact with one another at a core forming station 820. Upper layer material 280 is provided by upper layer mechanism 2800, and lower layer material 282 is provided by lower layer mechanism 2820. The central fibrous layer is prepared at the core forming station 820, and the at least one additional layer 286 is supplied to core forming station 820 via cut-and-place apparatus 400.

Any cut-and-place apparatus 400 capable of cutting a material from a moving web at a first speed, and placing it on another moving web at a second speed different from the first speed can be used in the present invention. Suitable cut-and-place apparatus are disclosed in, inter alia, U.S. Pat. No. 6,165,306, 6,149,755, 6,095,218, 6,074,333, 6,059,710, and 5,415,716, the disclosures of each of which are incorporated by reference herein in their entireties. The simplified cut-and-place apparatus illustrated in FIG. 4 includes a feed roller system 410 that feeds a web of material containing the at least one additional layer 286 at a first speed to the cut-and-place apparatus 400. Those skilled in the art will recognize that feed roller system 410 may be comprised of any number of component parts, such as a supply reel, a plurality of dancer rolls and edge guide rolls, and pull rolls to establish the first speed of the web material.

Figure 4:
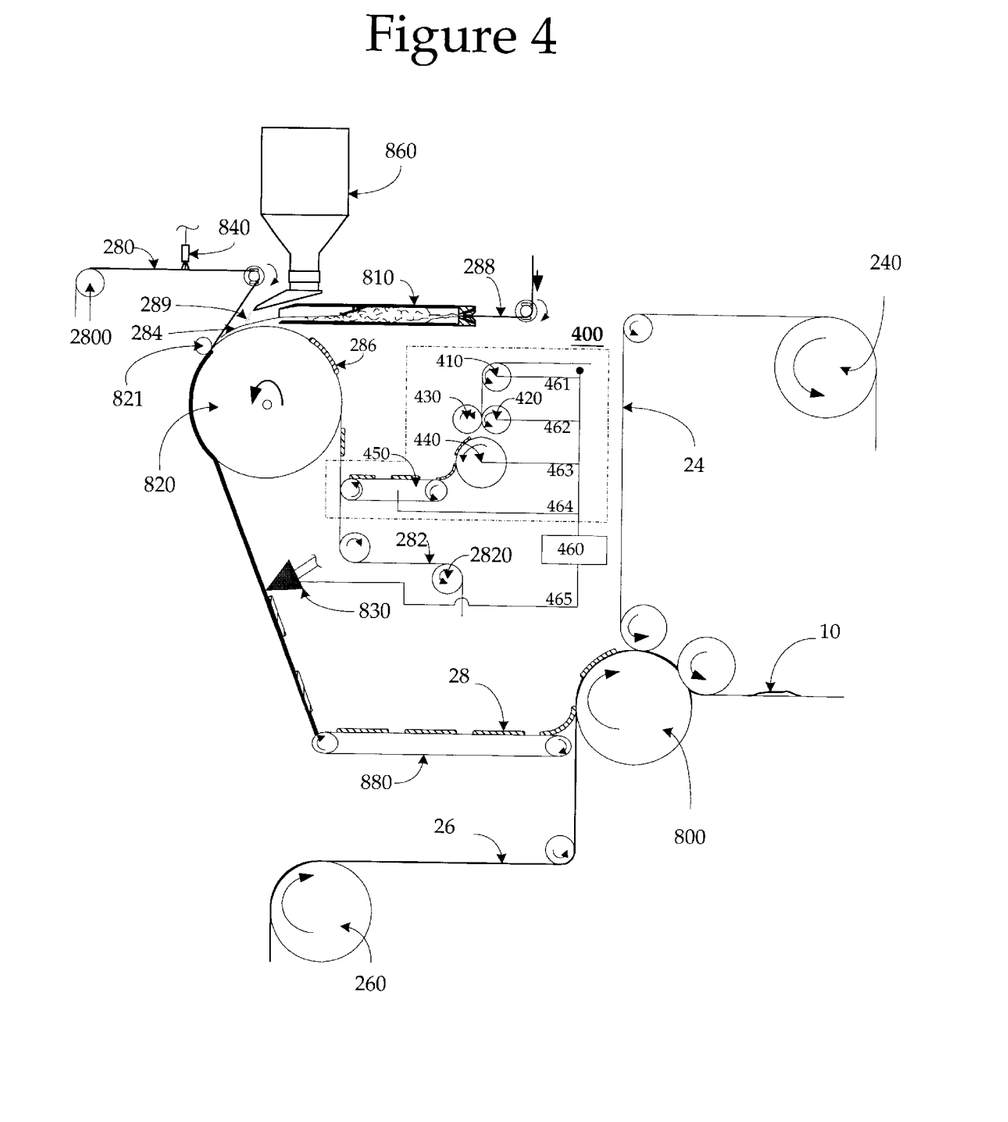
FIG. 4 is an illustration of an apparatus and method useful in forming an absorbent composite core, and in forming an absorbent garment.

Feed roller system 410 feeds the web of material to a cutting station, illustrated in FIG. 4 as a pair of rollers in cutting engagement with one another. Any type of cutting device can be used in the present invention that is capable of controlled cutting of a moving web of material. FIG. 4 shows a rotatable knife roll 420 in cutting engagement with a rotatable anvil roll 430. The knife roll can be controlled to control cutting the web at the appropriate locations to form an appropriately sized additional layer 286.

Upon cutting, the at least one additional layer 286 is placed on a rotatable vacuum transfer drum 440 that alters the velocity of the moving web to the second speed so as to control its placement on, for example, lower layer 282, which is moving at a speed different from the speed at which the web containing the at least one additional layer 286 is fed to cut-and-place apparatus 400. The rotatable vacuum transfer drum 440 can be any type of rotating drum capable of drawing a vacuum so that it can grab onto and hold the now severed additional layer 286, and ultimately transfer it to moving lower layer 282 via additional layer conveyor 450, for example. In this embodiment, additional layer conveyor 450 transports the additional layer 286 at the second speed to the moving web. Skilled artisans will appreciate, however, that rotatable vacuum transfer drum 440 could deposit the additional layer 286 on lower layer 282 or upper layer 280, without the use of the additional layer conveyor 450.

The cut-and-place apparatus 400 can be controlled by controller 460. Controller 460 monitors and controls the first speed at which the moving web is conveyed by monitoring and controlling feed roller system 410 via control 461, and by monitoring and controlling knife roll 420 and anvil roll 430 via control 462. Controller 460 also monitors and controls the second speed at which the severed additional layer 286 is conveyed by monitoring and controlling the rotatable vacuum transfer drum 440 via control 463, the additional layer conveyor 450 via control 464, and by monitoring cutting knife 830 via control 465. Those skilled in the art will recognize that various modifications may be made to controller 460 to adequately control the first and second speeds such that the at least one additional layer 286 is accurately placed on moving lower layer 282 (or upper layer 280), and that any control system capable of such control can be used in the present invention. Using the guidelines provided herein, those skilled in the art are capable of designing a suitable controller 460 without undue experimentation.

FIG. 4 illustrates the additional layer 286 being disposed on the interior side of lower layer 282, e.g., the side that will be on the interior of the absorbent composite core 28, but the invention is in by no means limited to this particularly preferred embodiment and configuration. The additional layer could be disposed on the exterior side of lower layer 282 (i.e., when a softness layer is used), or one or more additional layer(s) could be disposed on the interior or exterior of upper layer 280, using a similar cut-and-place apparatus 400. In a similar fashion, one or more additional layer(s) 286 could be disposed on the interior or exterior of top sheet material 24, or back sheet material 26 using a similar cut-and-place apparatus 400.

After placing the at least one additional layer 286 in the appropriate position on lower layer 282, the lower layer and additional layer 286 are fed to core forming station 820 to form the absorbent composite core 28. Tow fibers 288 are mixed with SAP to form the central fibrous layer 284 at core forming station 820. Any type of tow fiber 288 can be supplied to the apparatus and, as conventional in the art, the tow fiber 288 typically is opened prior to forming a fibrous matrix. In this regard, the apparatus and method of the invention preferably includes a tow opener and feeder 810 that is capable of opening any suitable tow material, expanding the tow fiber and feeding the tow fiber to the core forming station 820. Any suitable tow opener and feeder 810 can be used in the method of the invention.

The tow fibers 288 preferably are mixed with superabsorbent polymer (SAP) material 289 to form central absorbent layer 284. The SAP is fed to the core forming station 820 by any SAP feeder 860 capable of feeding the SAP to the core forming station 820. Those skilled in the art are capable of designing a suitable SAP feeder 860 and nozzle configuration (or other dispensing device capable of dispensing and dispersing the SAP in the tow fibers 288) to provide adequate mixing of SAP material 289 and tow fibers 288 to form central fibrous layer 284.

Absorbent composite core 28 can be formed at core forming station 820, where central fibrous layer 284, comprised of SAP material 289 and tow fibers 288, is disposed between an upper layer 280, and a lower layer 282. Upper and lower layers 280, 282 can be fed to core forming unit 820 using any supplying mechanism known in the art, and preferably are fed through one or more feed rollers 2800, 2820, respectively. Adhesive can be applied to either upper layer 280 or lower layer 282, or to both layers (or to neither layer) by an adhesive applicator 840. Again, any mechanism capable of supplying an adhesive, albeit a spray adhesive, or one that is "rubbed" on, can be used in the invention. Suitable adhesives include any adhesive commonly employed in absorbent garments that is useful in adhering one or more tissue and/or non-woven materials together. It is particularly preferred to use construction adhesives, including HL-1258 by H. B. Fuller Company of St. Paul, Minn.; Findley 2031 and H2587-01 by Ato Findley Inc. of Wauwatosa, Wis.; and NS34-5665 by National Starch Co. of Bridgewater, N.J. Other adhesives that may be used in the invention include 34-578A, available from National Starch Co. of Bridgewater, N.J. Any of these adhesives may be used in all adhesive applications in the absorbent garment, or only in select applications as a construction adhesive for bonding parts of the garment as the top sheet, back sheet, absorbent core, and additional layer(s).

As the SAP material 289 and tow fibers 288 mix together to form central fibrous layer 284, which in turn is disposed between upper layer 280 and lower layer 282 at core forming station 820, some of these SAP particles may become affixed in the adhesive when the absorbent composite core 28 is passed through the one or more nip rollers 821 at the core forming station 820. The absorbent composite cores 28 then are cut to length by cutting knife 830. Cutting knife 830 can be any suitable cutting device capable of cutting absorbent composite core 28 of the invention. For example, cutting knife 830 can be comprised of a set of rollers; one being an anvil, and another having a knife attached at one point on the roller, whereby the diameter of the roller is selected to coordinate with the speed at which absorbent composite cores 28 are formed. The knife roller and anvil roller then can rotate at the same speed as the line speed to cut the absorbent composite core 28 at select areas to form uniform length cores 28. Skilled artisans are capable of designing a suitable cutting knife 830 given the specifics of each article forming assembly line.

After forming the absorbent composite core 28, the cores can be stored for later use, or immediately used as a component part of an absorbent garment. Preferably, the absorbent composite core 28 is used immediately as a component part of an absorbent garment. In this context, the absorbent composite cores 28 then would be transported to garment forming station 800 via core conveyor 880 (or any other conveying device) where they will be disposed between a top sheet 24 and a back sheet 26.

Top sheet material 24 may be supplied to forming station 800 by top sheet supply mechanism 240, which can be any supply mechanism capable of supplying top sheet 24 to garment forming station 800. Preferably, top sheet material 24 is supplied via a supply roller 240 and select feed or guide rollers. Back sheet material 26 likewise can be supplied to forming station 800 by back sheet supply mechanism 260, which can be any supply mechanism capable of supplying back sheet 26 to garment forming station 800. Preferably, back sheet material 26 is supplied via a supply roller 260 and select feed or guide rollers. Forming station 800 brings together the respective components of absorbent article 10 by disposing absorbent composite core 28 between top sheet material 24, and back sheet material 26. The final absorbent article 10 then may be cut and folded to the appropriate size and shape downstream from forming station 800.

The embodiment illustrated in FIG. 4 could include a number of additional devices used in preparing absorbent garments. For example, it is conventional to employ leg elastics 30, and standing leg gathers 40. Leg elastics 30 could be supplied to garment forming station 800 by any suitable manner known in the art. It is conventional to apply adhesives to either the leg elastics 30 themselves, or to apply adhesives on back sheet 26 or top sheet 24, and then dispose the leg elastics 30 there between. The leg elastics 30 may be supplied as an elastic element, or as a laminate of elastic elements disposed between two outer layers, preferably outer nonwoven materials.

Standing leg gathers 40 can be applied as a separate material to top sheet 24, and disposed on the exterior facing side (e.g., body facing side) of the top sheet. The standing leg gathers can be applied either prior to, or downstream from, garment forming station 800 using techniques known in the art.

Fastening elements 34 also can be supplied and attached to garment 10 either prior to or downstream from garment forming station 800. It is preferred that fastening elements are secured to garment 10 after garment forming station 800. It also is preferred that fastening elements 34 include fasteners 36, which can be applied before or after fastening elements 34 are attached to garment 10.

Additional layers also may be placed on garment 10 after forming station 800, or disposed between top sheet 24 and back sheet 26 by supplying the additional layer(s) to garment forming station 800. These additional layer(s) also may be cut-and-placed on top sheet 24 and/or back sheet 26 using cut-and-place apparatus 400.

It also is typical in the industry to include a waist elastic system comprising one or more waist elastic materials 32. Waist elastics 32 preferably are supplied upstream of garment forming station 800, and thus disposed between the top sheet 24 and back sheet 26. Waist elastics 32 may, however, be supplied downstream from garment forming station 800, and an outer cover or backing sheet (not shown) disposed outside the back sheet 26, using techniques known in the art. The waist elastic elements 32 may be supplied as a layer of material, or as elastic elements disposed between two outer materials. In a similar fashion, tummy elastics (not shown) may be supplied prior to, or downstream from garment forming station 800.

Figure 3:
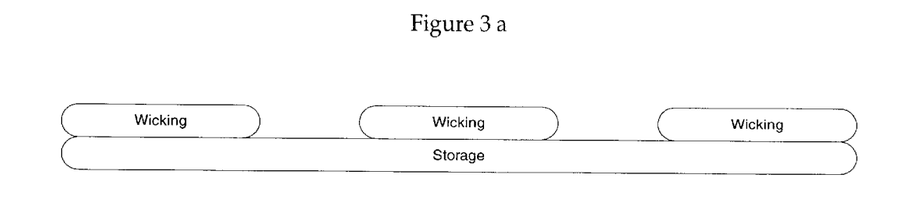
FIGS. 3a–3g are cross-sectional views of various embodiments of an absorbent composite core made in accordance with the present invention.

The method and apparatus of the invention are suitable for making absorbent composite cores 28 that include at least an upper layer 282, a lower layer 280, a central fibrous layer 284 (or storage layer), and at least one additional layer 286. Various configurations of the respective components of absorbent composite core 28 are shown in FIGS. 3a–3g, with the upper and lower layers (282, 280) removed for purposes of clarity. FIG. 3a shows an absorbent composite core including a central fibrous layer 284 (storage layer), and a fragmented wicking layer 286, that is comprised of three fragments disposed separately across the lateral width of absorbent composite core 28.

FIG. 3b illustrates another embodiment of an absorbent composite core 28 that can be made by the method and apparatus of the invention. Here, a central fibrous layer 284 (storage layer) is included with six (6) laterally fragmented layers: three (3) fragmented acquisition layers; and three (3) fragmented wicking layers. The fragmented acquisition layers and wicking layers can be strategically placed above the storage layer to provide improved fluid acquisition and storage, thereby reducing leakage. FIG. 3c shows a similar arrangement, only here the storage layer is fragmented as well.

FIGS. 3d–3g represent a few other possible configurations of absorbent composite cores 28 that can be made by the method and apparatus of the invention. Those skilled in the art will appreciate that numerous other configurations are contemplated by the present invention. Indeed, the method and apparatus of the invention provide considerable flexibility in making a variety of absorbent composite cores 28 to provide a variety of different properties.

Other embodiments, uses, and advantages of the invention will be apparent to those skilled in the art from consideration of the specification and practice of the invention disclosed herein. The specification should be considered exemplary only, and the scope of the invention is accordingly intended to be limited only by the following claims.

What is claimed is:

1. A method of making an absorbent composite core comprising:
   providing an upper layer to a core forming station;
   providing a lower layer to a core forming station;
   providing at least one additional layer;
   cutting the at least one additional layer and placing it on a surface of the upper layer or lower layer prior to forming the core; and
   forming the absorbent composite core at the core forming station by forming a central fibrous layer comprising a mixture of tow fibers and superabsorbent polymer material (SAP) and disposing the central fibrous layer between the upper layer and the lower layer so that it contacts the at least one additional layer.

2. The method of claim 1, wherein the at least one additional layer is selected from the group consisting of a fluid acquisition layer, a distribution layer, an additional fibrous layer optionally containing SAP, a wicking layer, a storage layer, a dryness layer, a softness layer, and combinations and fragments thereof.

3. The method of claim 1, wherein one additional layer is used, and the layer is a fluid acquisition layer.

4. The method of claim 1, wherein one additional layer is used, and the layer is a distribution layer.

5. The method of claim 1, wherein one additional layer is used, and the layer is an additional fibrous layer containing SAP.

6. The method of claim 1, wherein one additional layer is used, and the layer is a wicking layer.

7. The method of claim 1, wherein one additional layer is used, and the layer is a storage layer.

8. The method of claim 1, wherein one additional layer is used, and the layer is a fragmented layer.

9. The method of claim 1, wherein one additional layer is used, and the layer is a combination of a wicking layer and a distribution layer.

10. The method of claim 1, wherein two additional layers are used.

11. The method of claim 1, wherein the central fibrous layer comprises from about 30% to about 95% by weight super absorbent polymer (SAP).

12. The method of claim 1, wherein the central fibrous layer comprises cellulose ester tow fibers.

13. The method of claim 12, wherein the tow fibers are cellulose acetate tow fibers.

14. The method of claim 1, wherein the upper and lower layer are comprised of the same material, and the material is selected from the group consisting of tissue, airlaid fluff pulp, synthetic non-woven material, and mixtures or combinations thereof.

15. The method of claim 14, wherein the upper layer is fluid pervious, and the lower layer is fluid impervious.

16. The method of claim 1, wherein the central fibrous layer further comprises up to 10% by weight fluff wood pulp fibers.

17. The method of claim 1, wherein the central fibrous layer further comprises particulate additives.

18. The method of claim 1, wherein the at least one additional layer is provided prior to cutting at a first speed, and the upper layer or lower layer are provided to the core forming station at a second speed, the second speed being different from the first speed.

19. The method of claim 18, wherein the second speed is faster than the first speed.

20. A method of making an absorbent article comprising:
   a) providing a top sheet and a back sheet to a garment forming station;
   b) preparing an absorbent composite core by:
      b1) providing an upper layer to a core forming station;
      b2) providing a lower layer to a core forming station;
      b3) providing at least one additional layer;
      b4) cutting the at least one additional layer and placing it on a surface of the upper layer or lower layer prior to forming the core; and
      b5) forming the absorbent composite core at the core forming station by forming a central fibrous layer comprising a mixture of tow fibers and superabsorbent polymer material (SAP) and disposing the central fibrous layer between the upper layer and the lower layer so that it contacts the at least one additional layer;
   c) providing the absorbent composite core to the garment forming station; and
   d) disposing the absorbent composite core between the top sheet and the back sheet at the garment forming station.

21. The method of claim 20, whereby the absorbent garment is prepared such that the top sheet and the back sheet form a first waist region, a second waist region longitudinally opposite the first waist region, and a crotch region between the waist regions.

22. The method of claim 21, further comprising
   e) attaching at least one fastening element to lateral edges of the first waist region; and
   f) preparing at least one target device and attaching the at least one target device to the article in the second waist region, where the at least one fastening element and the at least one target device are capable of attaching to one another, the at least one target device being located so that the first waist region and second waist region of the article may be joined to one another to secure the article on a wearer.

23. The method of claim 22, wherein the at least one fastening element comprises a hook portion of a hook and loop fastener and the at least one target device comprises the loop portion of a hook and loop fastener.

24. The method of claim 22, wherein the at least one fastening element is an adhesive tape and the at least one target device comprises a tape receiving surface.

25. The method of claim 22, wherein the at least one fastening element is comprised of a pair of laterally extending tabs disposed on the lateral edges of the first waist region, whereby the laterally extending tabs each include at least one fastening element.

26. The method of claim 20, wherein the at least one additional layer is selected from the group consisting of a fluid acquisition layer, a distribution layer, an additional fibrous layer optionally containing SAP, a wicking layer, a storage layer, a dryness layer, a softness layer, and combinations and fragments thereof.

27. The method of claim 20, wherein one additional layer is used, and the layer is a fluid acquisition layer.

28. The method of claim 20, wherein one additional layer is used, and the layer is a distribution layer.

29. The method of claim 20, wherein one additional layer is used, and the layer is an additional fibrous layer containing SAP.

30. The method of claim 20, wherein one additional layer is used, and the layer is a wicking layer.

31. The method of claim 20, wherein one additional layer is used, and the layer is a storage layer.

32. The method of claim 20, wherein one additional layer is used, and the layer is a fragmented layer.

33. The method of claim 20, wherein one additional layer is used, and the layer is a combination of a wicking layer and a distribution layer.

34. The method of claim 20, wherein two additional layers are used.

35. The method of claim 20, wherein the central fibrous layer comprises from about 30% to about 95% by weight super absorbent polymer (SAP).

36. The method of claim 20, wherein the central fibrous layer comprises, cellulose ester tow fibers.

37. The method of claim 36, wherein the tow fibers are cellulose acetate tow fibers.

38. The method of claim 20, wherein the upper and lower layer are comprised of the same material, and the material is selected from the group consisting of tissue, airlaid fluff pulp, synthetic non-woven material, and mixtures or combinations thereof.

39. The method of claim 38, wherein the upper layer is fluid pervious, and the lower layer is fluid impervious.

40. The method of claim 20, wherein the central fibrous layer further comprises up to 10% by weight fluff wood pulp fibers.

41. The method of claim 20, wherein the central fibrous layer further comprises particulate additives.

42. The method of claim 20, wherein the at least one additional layer is provided prior to cutting at a first speed, and the upper layer or lower layer are provided to the core forming station at a second speed, the second speed being different from the first speed.

43. The method of claim 42, wherein the second speed is faster than the first speed.

44. An apparatus for forming an absorbent composite core comprising:
   a composite core forming station;
   an upper layer supply mechanism for supplying an upper layer material to the composite core forming station;
   a lower layer supply mechanism for supplying a lower layer to the composite core forming station;
   a central fibrous layer making device for making the central fibrous layer by mixing tow fibers and super-absorbent polymer material (SAP), and for supplying the central fibrous layer to the core forming station; and
   a cut-and-place apparatus for effecting cutting of at least one additional layer that is supplied to the cut-and-place apparatus at a first speed, and placing the cut additional layer(s) on either the upper layer or lower layer at a second speed prior to forming the central fibrous layer,
   whereby the respective components are positioned relative to one another such that the central fibrous layer is disposed between the upper layer and the lower layer at the core forming station and contacts the at least one additional layer.

45. The apparatus of claim 44, whereby the second speed is different from the first speed.

46. The apparatus of claim 45, wherein the second speed is faster than the first speed.

47. The apparatus of claim 44, wherein the cut-and-place apparatus comprises:
   a feed roller system for feeding a web containing the at least one additional layer to the cut-and-place apparatus at a first speed;
   a cutting station to cut the web containing the at least one additional layer into discrete additional layers; and
   a rotatable vacuum transfer drum for transferring the cut discrete additional layers at a second speed and placing the discrete additional layers on either the upper layer or lower layer.

48. The apparatus of claim 47, wherein the feed roller system comprises one or more dancer rolls, edge guide rolls, and pull rolls.

49. The apparatus of claim 47, wherein the cutting station comprises a knife roller and an anvil roller.

50. The apparatus of claim 47, further comprising a controller capable of controlling the first speed and the second speed to adequately cut-and-place the at least one additional layer on the upper layer or tower layer.

51. The apparatus of claim 47, further comprising an additional layer conveyor for placing the cut discrete additional layers on either the upper layer or the lower layer.

52. An apparatus for forming an absorbent garxnent comprising:
   a garment forming station;
   a top sheet supply mechanism for supplying a top sheet material to the garment forming station;
   a back sheet supply mechanism for supplying a back sheet material to the garment forming station;
   an apparatus for making a composite absorbent core that comprises:
      a composite core forming station;
      an upper layer supply mechanism for supplying an upper layer material to the composite core forming station;
      a lower layer supply mechanism for supplying a lower layer to the composite core forming station;
      a central fibrous layer making device for making the central fibrous layer by mixing tow fibers and super-absorbent polymer material (SAP), and for supplying the central fibrous layer to the core forming station; and
      a cut-and-place apparatus for effecting cutting of at least one additional layer that is supplied to the cut-and-place apparatus at a first speed, and placing the cut additional layer(s) on either the upper layer or lower layer at a second speed prior to forming the central fibrous layer;

whereby the respective components are positioned relative to one another such that the central fibrous layer is disposed between the upper layer and the lower layer at the core forming station and contacts the at least one additional layer; and an absorbent composite core feed mechanism for feeding the absorbent composite core to the garment forming station, whereby the respective components are arranged such that the absorbent composite core is disposed between the top sheet material and the back sheet material at the garment forming station.

53. The apparatus of claim 52, further comprising an elastic supply mechanism for feeding a supply of elastic material to the garment forming station.

54. The apparatus of claim 52, further comprising a mechanism for feeding a fastening element to the absorbent garment after garment forming station, and for attaching the fastening element to the absorbent garment.

55. The apparatus of claim 52, further comprising a mechanism for feeding a standing leg gather to the absorbent garment after garment forming station, and for attaching the standing leg gather to the absorbent garment.

56. The apparatus of claim 52, further comprising a mechanism for feeding a waist elastic material to the absorbent garment prior to garment forming station.

57. The apparatus of claim 52, whereby the second speed is different from the first speed.

58. The apparatus of claim 57, wherein the second speed is faster than the first speed.

59. The apparatus of claim 52, wherein the cut-and-place apparatus comprises:

a feed roller system for feeding a web containing the at least one additional layer to the cut-and-place apparatus at a first speed;

a cutting station to cut the web containing the at least one additional layer into discrete additional layers; and a rotatable vacuum transfer drum for transferring the cut discrete additional layers to either the upper layer or the lower layer at a second speed.

60. The apparatus of claim 59, wherein the feed roller system comprises one or more dancer rolls, edge guide rolls, and pull rolls.

61. The apparatus of claim 59, wherein the cutting station comprises a knife roller and an anvil roller.

62. The apparatus of claim 59, further comprising a controller capable of controlling the first speed and the second speed to adequately cut-and-place the at least one additional layer on the upper layer or lower layer.

63. The apparatus of claim 59, further comprising an additional layer conveyor for placing the cut discrete additional layers on either the upper layer or the lower layer.

\* \* \* \* \*